US009816951B2

(12) United States Patent
Dyshlyuk et al.

(10) Patent No.: US 9,816,951 B2
(45) Date of Patent: Nov. 14, 2017

(54) METHOD FOR DETERMINING A VOLUME THERMAL EXPANSION COEFFICIENT OF A LIQUID

(71) Applicant: Schlumberger Technology Corporation, Sugar Land, TX (US)

(72) Inventors: Evgeny Nikolaevich Dyshlyuk, Moscow (RU); Albina Rishatovna Mutina, Bogota (CO); Simon Ivar Andersen, Edmonton (CA); Kurt Schmidt, Oxford (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 431 days.

(21) Appl. No.: 14/320,638

(22) Filed: Jun. 30, 2014

(65) Prior Publication Data
US 2015/0036715 A1    Feb. 5, 2015

(30) Foreign Application Priority Data

Jul. 30, 2013  (RU) .............................. 2013135668

(51) Int. Cl.
*G01K 5/00*         (2006.01)
*G01N 25/16*        (2006.01)
(Continued)

(52) U.S. Cl.
CPC ............. *G01N 25/16* (2013.01); *G01N 25/20* (2013.01); *G01N 25/4866* (2013.01); *G01N 33/18* (2013.01); *G01N 33/28* (2013.01)

(58) Field of Classification Search
CPC ........ G01K 17/00; G01K 17/06; G01K 13/00; G01K 25/00; G01K 25/20; G01K 5/00; G01N 25/16; C04B 2235/9607
(Continued)

(56) References Cited

U.S. PATENT DOCUMENTS 3,527,081 A    9/1970  Hill
4,055,982 A *  11/1977  Ter-Minassian ... G01N 25/4866
                                                    374/10
(Continued)

FOREIGN PATENT DOCUMENTS

RU     2076313 C1    3/1997
SU      712745 A1    1/1980
(Continued)

OTHER PUBLICATIONS

J. C. G. Calado, et al. "Experimental and theoretical study of the equation of state of liquid ethylene," Journal of Chemical & Engineering Data 1982, 27, pp. 376-385.
(Continued)

*Primary Examiner* — Gail Kaplan Verbitsky

(57) ABSTRACT

In order to determine a volume thermal expansion coefficient of a liquid, a sample of the liquid is placed inside a cell of a calorimeter followed by an incremental increase of pressure inside the cell containing the liquid. After each pressure increase heat flow into the cell and volume of the liquid are measured. Based on results of the measurements of the heat flow and accounting for initially evaluated cell volume, the volume thermal expansion of the liquid is determined.

5 Claims, 4 Drawing Sheets

(51) Int. Cl.
*G01N 25/20* (2006.01)
*G01N 25/48* (2006.01)
*G01N 33/18* (2006.01)
*G01N 33/28* (2006.01)

(58) Field of Classification Search
USPC .... 374/29–39, 45, 55, 46, 143, 54, 1, 3, 43; 422/51; 436/147
See application file for complete search history.

(56) References Cited

U.S. PATENT DOCUMENTS

| | | | |
|---|---|---|---|
| 5,988,875 | A | 11/1999 | Gershfeld et al. |
| 6,488,406 | B2 | 12/2002 | Danley |
| 6,869,214 | B2 | 3/2005 | Plotnikov et al. |
| 7,350,971 | B2 | 4/2008 | Williams et al. |
| 7,455,449 | B2 | 11/2008 | Nishimura |
| 9,080,934 | B2 * | 7/2015 | Nadeev .................. G01N 15/08 |
| 2002/0034210 | A1 * | 3/2002 | Plotnikov .............. G01K 17/00 374/10 |
| 2004/0024542 | A1 * | 2/2004 | Plotnikov .......... G01N 25/4806 702/31 |
| 2013/0135668 | A1 | 5/2013 | Minagawa |
| 2013/0344612 | A1 * | 12/2013 | Zuo .................... G01N 25/4806 436/147 |

FOREIGN PATENT DOCUMENTS

| | | |
|---|---|---|
| SU | 813223 A1 | 3/1981 |
| SU | 1065752 A1 | 1/1984 |

OTHER PUBLICATIONS

L. A. Davis, et al., "Compression of Mercury at High Pressure," Journal of Chemical Physics, 1967, 46 (7), pp. 2650-2660.

S. L. Randzio, J.-P. E. Grolier and J. R. Quint, "Thermal expansivities of n-hexane,n-hexanol and their mixtures over the temperature range from 303 K to 503 K at pressures up to 400 MPa," Journal of Thermal Analysis and Calorimetry vol. 38 (1992), pp. 1959-1963.

K. L. Ramakumar, et al., "Experimental Evaluation of Procedures for Heat Capacity Measurement by Differential Scanning Calorimetry" Journal of Thermal Analysis and Calorimetry, V.66, Issue 2, 2001, pp. 387-397.

P. Pruzan, L. Ter Minassian, P. Figuiere, H. Szwarc "High Pressure calorimetry as applied to piezothermal analysis," Review of Scientific Instruments, vol. 47, No. 1, Jan. 1976.

S. Verdier, S. Andersen, "Determination of Isobaric Thermal Expansivity of Organic Compounds from 0.1 to 30 MPa at 30 degrees C with an Isothermal Pressure Scanning Microcalorimeter," Journal of Chemical and Engineering Data, 2003, vol. 48, No. 4, pp. 892-897.

J. Troncoso, P. Navia, L. Romani, et.al. "On the isobaric thermal expansivity of liquids". The Journal of Chemical Physics 134, 094502. 2011.

* cited by examiner

METHOD FOR DETERMINING A VOLUME THERMAL EXPANSION COEFFICIENT OF A LIQUID

CROSS-REFERENCE TO RELATED APPLICATION

This application claims priority to Russian Application No. 2013135668 filed Jul. 30, 2013, which is incorporated herein by reference in its entirety.

BACKGROUND

The invention deals with studies of properties of liquids which can be applied to numerous industries such as oil, gas and chemical industry.

The volume thermal expansion coefficient (VTEC or $\alpha$) is a physics value describing a relative change in a body volume due to temperature increase by one degree at a constant pressure:

$$\alpha = \frac{1}{V}\left(\frac{dV}{dT}\right)_p,$$

where V is the volume, T is the temperature, and p is the pressure. VTEC has a dimension inverse to temperature.

VTEC is an important thermodynamic parameter describing properties of liquids. This parameter is often required to describe models of liquids, for example, to simulate properties of oil and gas deposits in oil industry. For a given liquid VTEC depends on temperature and pressure. At the same time, VTEC measurements are often carried out at atmospheric pressure when the temperature does not match the required value.

Various techniques are used to measure VTEC: measurements of density of a liquid at different temperatures and pressures with subsequent interpretation of results obtained (Calado, J. C. G.; Clancy, P. Heintz, A. Streett, W. B. Experimental and theoretical study of the equation of state of liquid ethylene. J. Chem. Eng. Data 1982, 27, 376-385), measurements of sound velocity in a liquid (Davis, L. A.; Gordon, R. B. Compression of mercury at high pressure, J. Chem. Phys. 1967, 46 (7), 2650-2660). The above methods have low accuracy.

More precise information on VTEC can be obtained from measurements using a differential scanning calorimeter (DSC).

U.S. Pat. No. 6,869,214 B2 describes a method of measuring VTEC in a liquid solution using DSC. The method does not take into account influence of thermal effects associated with expanding material of a calorimeter cell during VTEC measurements; change of the cell effective volume when the pressure changes during VTEC measurements is also not taken into account, which reduces accuracy of VTEC obtained.

SUMMARY

The invention provides for improving accuracy of VTEC measurements using DSC at different temperatures and pressures due to taking into account influence of changing volume of a liquid inside a cell when the pressure increases.

The method comprises placing a sample of a liquid having known volume heat capacity into a cell of a calorimeter. Pressure in the cell containing the sample of the liquid is increased step-by-step. Heat capacity of the sample of the liquid for each pressure is measured and an effective volume of the cell is calculated. Then, a sample of a liquid being studied is placed into the calorimeter cell and pressure is step-by step increased inside the cell by injecting the liquid being studied.

After each pressure change a heat flow into the cell is measured; based on results of measurements of the heat flow and accounting for VTEC of the cell material and the effective cell volume, a volume thermal expansion coefficient is determined for the liquid being studied.

After each step of pressure increase the cell with the sample of the liquid being studied can be kept till stabilization of the heat flow.

The volume thermal expansion coefficient $\alpha$ of the liquid being studied is expressed as $$\alpha = \alpha_c + \frac{\delta Q}{dPV(p)T},$$

where $\alpha_c$—is a volume thermal expansion coefficient of a material from which the calorimeter cell is made,
$\delta Q$ is the heat effect determined after each step of pressure increase,
dP—is a pressure increase at each step,
V(p)—is the effective volume of the cell.

Oil, water, and saline solution can be used as liquids being studied.

BRIEF DESCRIPTION OF DRAWINGS

The invention is illustrated by drawings where.

DETAILED DESCRIPTION

Figure 1:
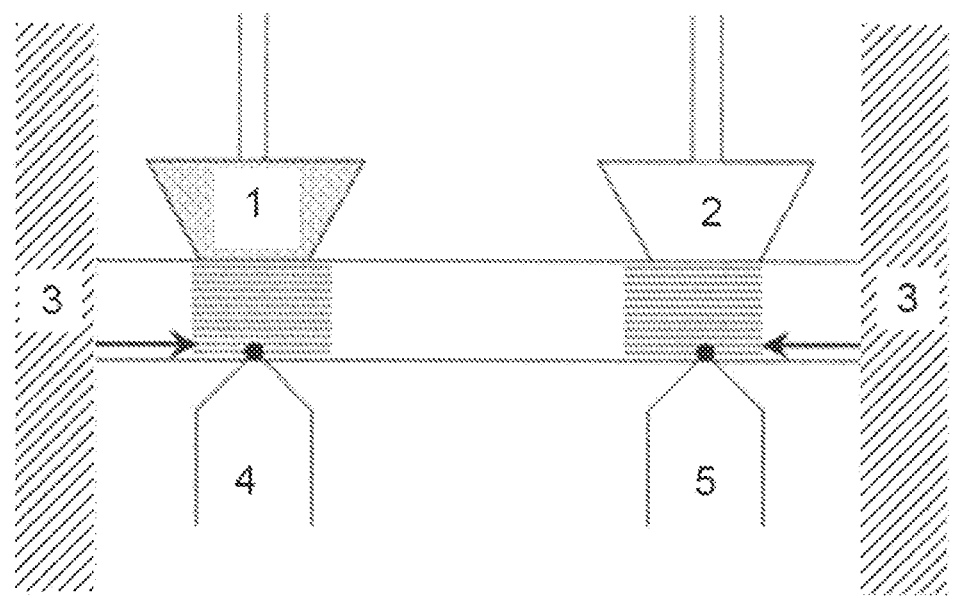
FIG. 1 shows a schematic diagram of a typical differential scanning calorimeter.

A typical differential scanning calorimeter (see FIG. 1) has two cells, one of which (cell 1) contains a sample being studied. The other cell 2 is a reference cell; depending on experiment it can remain empty or be filled. The cells have reliable heat insulation; they are kept at a controlled temperature which can be changed using a heater 3 of the calorimeter. Measurements of the temperature differential between each cell and the calorimeter chamber usually involve thermocouples 4 and 5. The accurate calibration of the calorimeter enables calculating heat flow differential between the calorimeter cells and the calorimeter chamber. Integrating heat flows in time allows determining the difference in amount of heat generated or absorbed in each cell. DSC instruments are able to operate at different temperatures (the temperature range depends on the calorimeter model); some DSC models can be equipped with cells that allow measurements at elevated pressures. To conduct the measurements it is necessary to combine DSC with the system capable of developing controlled pressure inside the calorimeter cells. Such system can be equipped with various types of pumps combined with pressure sensors; a piping can be used to connect the system to calorimeter cells.

In accordance to the method proposed to determine VTEC a calibration procedure should be conducted before studying the sample; the calibration helps to determine how volume of a liquid changes as a function of pressure. A sample of a liquid having known characteristics (e.g., n-hexane in S. L. Randzio, J.-P. E. Grolier and J. R. Quint, j. Thermal Anal., 38 (1992) 1959) is placed into the cell 1 of the calorimeter followed by pressure increase. The heat capacity of the sample is measured at a stable pressure level. This is followed by changing the pressure and repeating the measurement of heat capacity (see, for example, "Experimental evaluation of procedures for heat capacity measurement by differential scanning calorimetry" Ramakumar K., Saxena M., Deb S. Journal of Thermal Analysis and calorimetry, V. 66, Iss. 2, 2001, pp. 387-397). The heat capacity $C_{ref}$ measured for each pressure is compared to the tabular data on specific heat capacity for the liquid at a given pressure $c_{ref\_table}$, then the calculation of an effective cell volume (coinciding with effective volume of the liquid in the cell) is carried out for each pressure $V(p) =_{ref}(p)/c_{ref\_table}(p)$.

Figure 2:
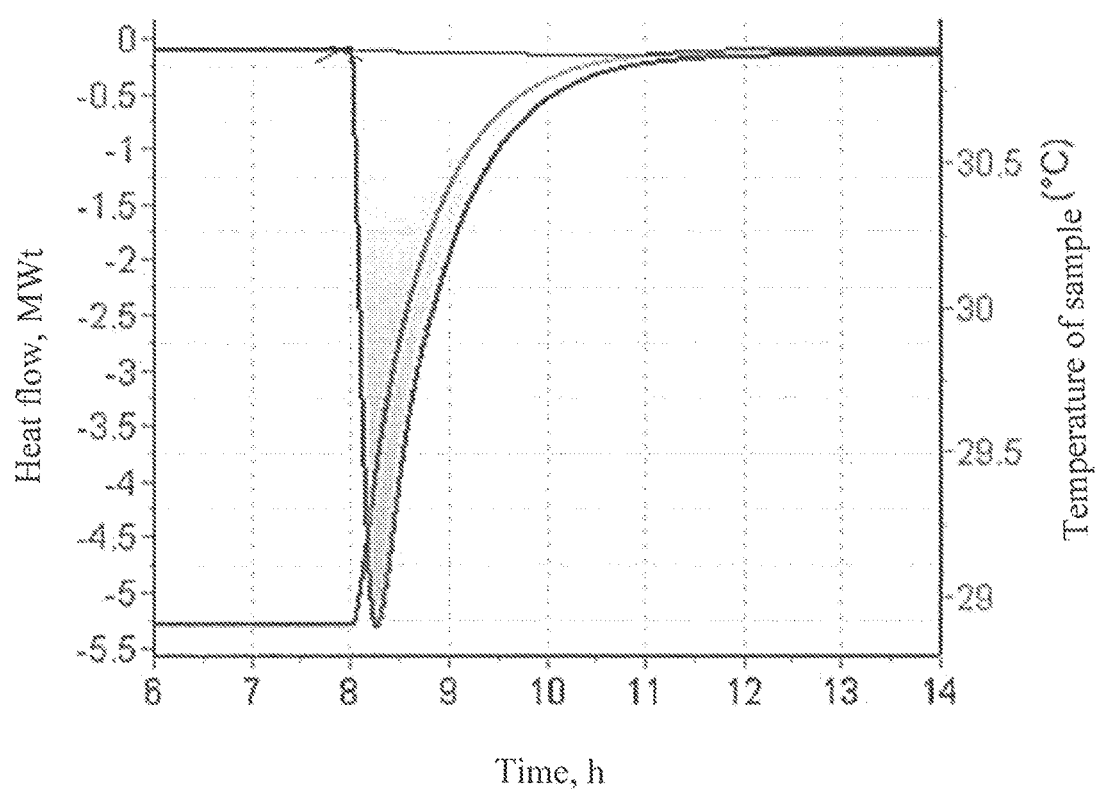
FIG. 2 illustrates profiles of temperature and heat flow.

In order to increase accuracy of measuring specific heat it is possible to use a method where temperature is changed in a step-like manner at each pressure, i.e. the method should have two isothermal intervals before and after temperature increase. The second interval should be long enough to ensure stabilizing the heat flow (see FIG. 2). The area between the curve of the heat flow FIG. 2 and the base line corresponds to the measured thermal effect.

After the calibration the cell 1 of the calorimeter is cleaned; then the cell is filled with a sample of a liquid being studied. After stabilization of heat flow (usually takes about 2 hours) pressure in the cell 1 is changed step-by-step by injection of the liquid being studied into the cell. After each pressure change the heat flow should be stabilized (hereinafter, the term "heat flow stabilization" implies reaching a stationary thermal regime when no absorption or generation of heat develops inside the cell; this regime is characterized by zero or base-line heat flow).

Figure 3:
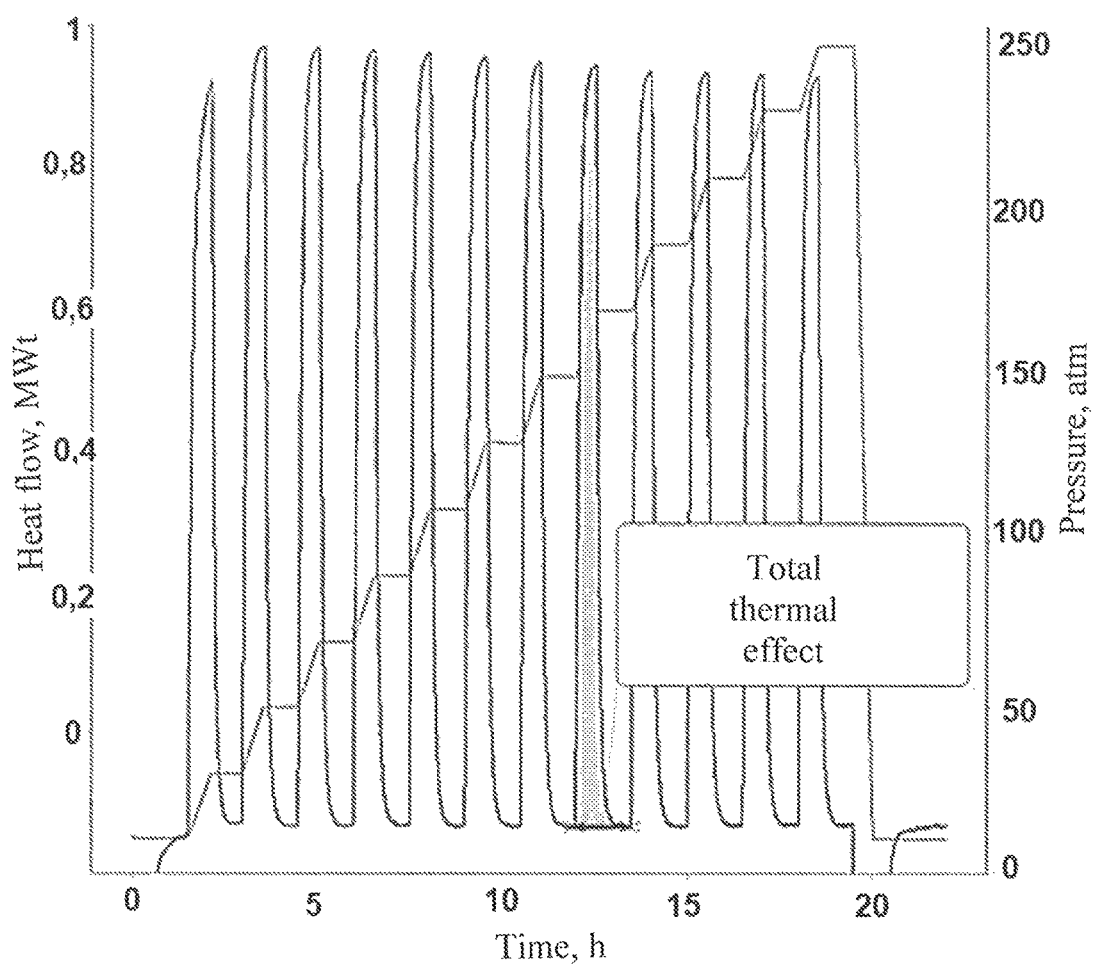
FIG. 3 shows a change in heat flow and thermal effect obtained during step-by-step pressure change.

The total heat flow (minus a baseline value corresponding to a signal when there is no pressure increase) allows evaluating a thermal effect δQ for each pressure as an area under the heat flow curve (see FIG. 3). In accordance with S. Verdier, S. I. Andersen "Determination of Isobaric Thermal Expansivity of Organic Compounds from 0.1 to 30 MPa at 30° C. with an Isothermal Pressure Scanning Microcalorimeter" the measured thermal effect is associated with VTEC (or α) in the liquid being studied, with VTEC $α_c$ of the cell material, with temperature T in the cell, with effective cell volume V(p) (i.e. when cell is filled with liquid), as well as with the step of pressure increase dP as follows:

$$δQ=(α-α_c)V(p)TdP,$$

Figure 4:
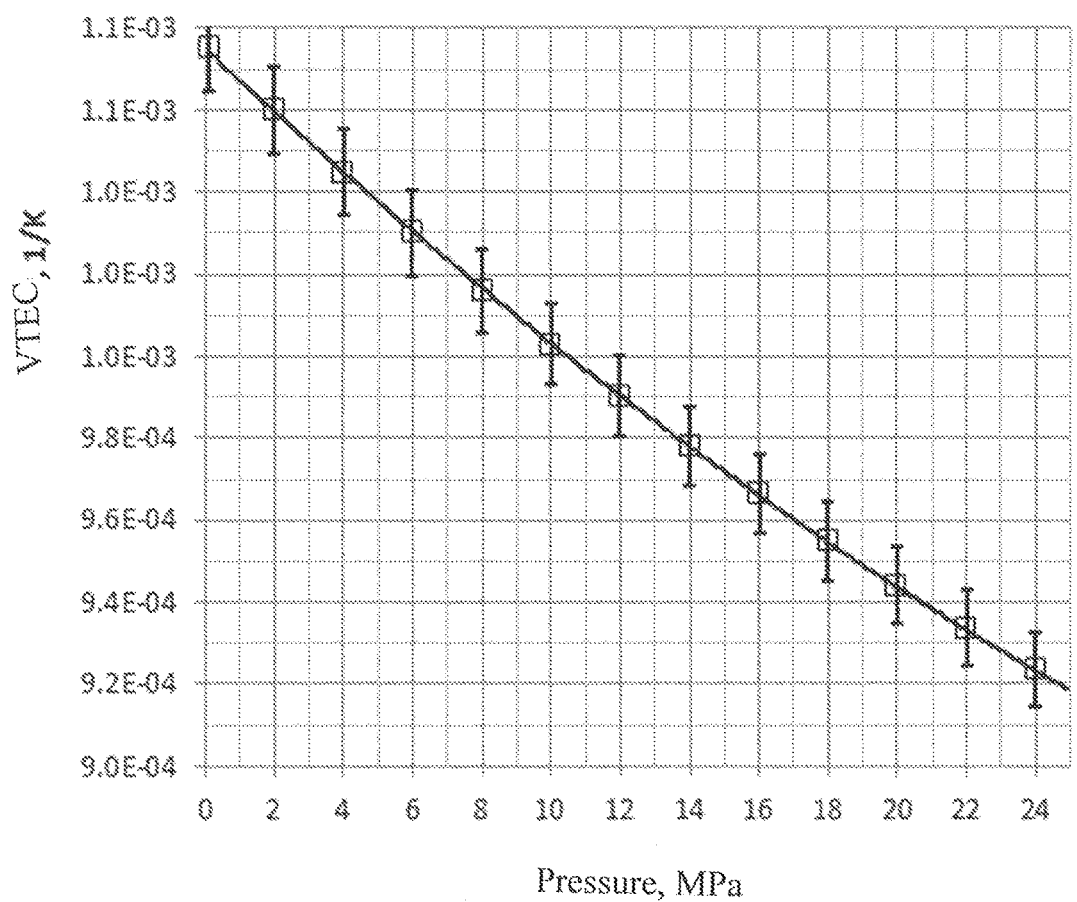
FIG. 4 shows volume thermal expansion coefficient at a fixed temperature for varying pressure.

A profile of VTEC changes as a function of pressure is a result of measurements made for each temperature (see, for example, FIG. 4).

As liquids being studied any liquid can be used, for example oil, water or salt.

The invention claimed is:

1. A method for determining a volume thermal expansion coefficient of a liquid comprising:
   placing a sample of a first liquid having a known volume heat capacity into a calorimeter cell,
   increasing a pressure inside the cell containing the sample of the first liquid having the known volume heat capacity and measuring a heat capacity of the sample at each pressure increase and calculating an effective cell volume,
   cleaning the calorimeter cell,
   placing a sample of a second liquid into the calorimeter cell,
   increasing a pressure inside the cell containing the sample of the second liquid by injecting the second liquid,
   measuring a heat flow into the cell after pressure increase; and
   determining the volume thermal expansion coefficient of the second liquid as $$α = α_c + \frac{δQ}{dPV(p)T},$$

where α is the volume thermal expansion coefficient of the second liquid,
$α_c$ is a volume thermal expansion coefficient of a material of the cell,
δQ is the heat effect determined after each pressure increase,
dP—is the pressure increase, and
V(p)—is the effective cell volume.

2. The method of claim 1, wherein oil is used as the second liquid.

3. The method of claim 1, wherein water is used as the second liquid.

4. The method of claim 1, wherein a salt solution is used as the second liquid.

5. The method of claim 1, wherein n-hexane is used as the first liquid.

* * * * *